United States Patent
Lord et al.

(10) Patent No.: US 8,496,638 B2
(45) Date of Patent: Jul. 30, 2013

(54) ABSORBENT ARTICLES HAVING A WAIST REGION AND CORRESPONDING FASTENERS THAT HAVE MATCHING STRETCH PROPERTIES

(75) Inventors: Patrick Robert Lord, Appleton, WI (US); Adrienne Nicole Hengels, Appleton, WI (US); Palani Raj Ramaswami Wallajapet, Neenah, WI (US); Catherine Marguerite Hancock-Cooke, Neenah, WI (US); Daniel Lee Ellingson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1488 days.

(21) Appl. No.: 10/881,017

(22) Filed: Jun. 30, 2004

(65) Prior Publication Data

US 2006/0004339 A1  Jan. 5, 2006

(51) Int. Cl.
*A61F 13/15* (2006.01)

(52) U.S. Cl.
USPC .................. 604/385.24; 604/385.22; 604/391

(58) Field of Classification Search
USPC ........... 604/385.22, 385.29–385.31, 389–391
See application file for complete search history.

(56) References Cited

U.S. PATENT DOCUMENTS

| | | | |
|---|---|---|---|
| 4,100,324 A | 7/1978 | Anderson et al. | |
| 4,253,461 A | 3/1981 | Strickland et al. | |
| 4,315,508 A | 2/1982 | Bolick | |
| 4,500,316 A | 2/1985 | Damico | |
| 4,655,760 A | 4/1987 | Morman et al. | |
| 4,657,802 A | 4/1987 | Morman | |
| 4,663,220 A | 5/1987 | Wisneski et al. | |
| 4,701,170 A | 10/1987 | Wilson et al. | |
| 4,704,115 A | 11/1987 | Buell | |
| 4,720,415 A | 1/1988 | Vander Wielen et al. | |
| 4,781,966 A | 11/1988 | Taylor | |
| 4,789,699 A | 12/1988 | Kieffer et al. | |

(Continued)

FOREIGN PATENT DOCUMENTS

| EP | 0323634 A2 | 7/1989 |
|---|---|---|
| EP | 0532034 B2 | 3/1993 |

(Continued)

OTHER PUBLICATIONS

Abstract of DE20310439, Oct. 23, 2003.

(Continued)

*Primary Examiner* — Lynne Anderson
(74) *Attorney, Agent, or Firm* — Dority & Manning, P.A.

(57) ABSTRACT

Absorbent articles with carefully controlled stretch properties are disclosed. In particular, the absorbent articles have a waistband that encompasses a pair of opposing side panels and a waist region of the article. The side panels are attached to longitudinal edges of a chassis and are configured to extend around a person's waist. The side panels are attached to fastening devices for fastening the absorbent article to a wearer. In accordance with the present invention, the side panels and the waist region are both elastic. In order to improve fit and comfort, the stretch properties of the side panels are matched with the stretch properties of the waist region. For example, elongation of the side panels can be matched to elongation of the waist region or, alternatively, displacement of the side panels can be matched to the displacement of the waist region for a given range of forces.

39 Claims, 6 Drawing Sheets

U.S. PATENT DOCUMENTS

| | | |
|---|---|---|
| 4,909,802 A | 3/1990 | Ahr et al. |
| 4,936,840 A | 6/1990 | Proxmire |
| 4,940,464 A | 7/1990 | Van Gompel et al. |
| 4,965,122 A | 10/1990 | Morman |
| 4,981,747 A | 1/1991 | Morman |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,151,092 A | 9/1992 | Buell et al. |
| 5,176,672 A | 1/1993 | Bruemmer et al. |
| 5,196,000 A | 3/1993 | Clear et al. |
| 5,224,405 A | 7/1993 | Pohjola |
| 5,226,992 A | 7/1993 | Morman |
| 5,242,436 A | 9/1993 | Weil et al. |
| 5,284,703 A | 2/1994 | Everhart et al. |
| 5,290,262 A | 3/1994 | Vukos et al. |
| 5,336,545 A | 8/1994 | Morman |
| 5,350,624 A | 9/1994 | Georger et al. |
| 5,358,500 A | 10/1994 | Lavon et al. |
| 5,368,584 A | 11/1994 | Clear et al. |
| 5,383,871 A | 1/1995 | Carlin et al. |
| 5,389,181 A | 2/1995 | Vukos et al. |
| 5,462,541 A | 10/1995 | Bruemmer et al. |
| 5,464,401 A | 11/1995 | Hasse et al. |
| 5,484,429 A | 1/1996 | Vukos et al. |
| 5,486,166 A | 1/1996 | Bishop et al. |
| 5,490,846 A | 2/1996 | Ellis et al. |
| 5,527,302 A | 6/1996 | Endres et al. |
| 5,542,942 A | 8/1996 | Kline et al. |
| 5,554,145 A | 9/1996 | Roe et al. |
| 5,634,916 A | 6/1997 | Lavon et al. |
| 5,645,542 A | 7/1997 | Anjur et al. |
| 5,653,704 A | 8/1997 | Buell et al. |
| 5,674,216 A | 10/1997 | Buell et al. |
| 5,749,866 A | 5/1998 | Roe et al. |
| 5,766,389 A | 6/1998 | Brandon et al. |
| 5,820,973 A | 10/1998 | Dodge, II et al. |
| 5,873,870 A | 2/1999 | Seitz et al. |
| 5,876,391 A | 3/1999 | Roe et al. |
| 5,938,652 A | 8/1999 | Sauer |
| 5,964,743 A | 10/1999 | Abuto et al. |
| 5,993,430 A | 11/1999 | Gossens et al. |
| 6,030,373 A | 2/2000 | VanGompel et al. |
| D422,078 S | 3/2000 | Vukos et al. |
| 6,045,543 A | 4/2000 | Pozniak et al. |
| 6,050,985 A | 4/2000 | Lavon et al. |
| 6,099,516 A | 8/2000 | Pozniak et al. |
| 6,132,411 A | 10/2000 | Huber et al. |
| 6,231,557 B1 | 5/2001 | Krautkramer et al. |
| 6,325,787 B1 | 12/2001 | Roe et al. |
| 6,362,389 B1 | 3/2002 | McDowall et al. |
| 6,406,466 B1 | 6/2002 | Pozniak et al. |
| 6,414,217 B1 | 7/2002 | Uitenbroek et al. |
| 6,454,888 B1 | 9/2002 | Murie et al. |
| 6,503,236 B1 | 1/2003 | Uitenbroek et al. |
| 6,552,245 B1 | 4/2003 | Roessler et al. |
| 6,582,412 B2 | 6/2003 | Christoffel et al. |
| 6,605,070 B2 | 8/2003 | Ludwig et al. |
| 6,641,568 B2 | 11/2003 | Ashton et al. |
| 6,645,190 B1 | 11/2003 | Olson et al. |
| 6,679,869 B1 | 1/2004 | Schlinz et al. |
| 6,682,512 B2 | 1/2004 | Uitenbroek et al. |
| 6,702,800 B1 | 3/2004 | Vukos et al. |
| 6,706,028 B2 | 3/2004 | Roe et al. |
| 6,726,670 B2 | 4/2004 | Almberg et al. |
| 6,730,069 B2 | 5/2004 | Tanzer et al. |
| 6,754,919 B2 | 6/2004 | Leaphart, Jr. et al. |
| 6,783,487 B2 | 8/2004 | Duhm et al. |
| 2002/0104608 A1 | 8/2002 | Welch et al. |
| 2002/0165516 A1* | 11/2002 | Datta et al. ............... 604/385.16 |
| 2002/0165517 A1 | 11/2002 | Datta et al. |
| 2002/0173768 A1 | 11/2002 | Elsberg et al. |
| 2003/0089453 A1 | 5/2003 | Tomsovic et al. |
| 2004/0015146 A1 | 1/2004 | Torigoshi et al. |
| 2004/0060648 A1 | 4/2004 | Thorson et al. |
| 2004/0060649 A1 | 4/2004 | Van Gompel et al. |
| 2004/0064121 A1 | 4/2004 | Van Gompel et al. |
| 2004/0122404 A1 | 6/2004 | Meyer et al. |
| 2005/0107764 A1* | 5/2005 | Matsuda et al. ............... 604/396 |

FOREIGN PATENT DOCUMENTS

| | | |
|---|---|---|
| EP | 1374814 A1 | 1/2004 |
| WO | WO 9948681 A1 | 9/1999 |
| WO | WO 0037009 A2 | 6/2000 |
| WO | WO 0037009 A3 | 6/2000 |
| WO | WO 0234185 A1 | 5/2002 |
| WO | WO 2004012640 A1 | 2/2004 |

OTHER PUBLICATIONS

Search Report and Written Opinion for PCT/US2005/017779, Sep. 1, 2005.

* cited by examiner

ABSORBENT ARTICLES HAVING A WAIST REGION AND CORRESPONDING FASTENERS THAT HAVE MATCHING STRETCH PROPERTIES

BACKGROUND OF THE INVENTION

Absorbent articles such as diapers, training pants, incontinence garments, swim undergarments, and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

Some of these absorbent articles contain various elastic materials to permit some expansion of the article when necessary to provide a better fit on the wearer. The elastic members are also designed to contract when being worn in order to provide the article with form-fitting properties at least in some areas.

For instance, some disposable diapers made in the past have included elastic fastener tabs that are typically joined to the rear portion of the article and are configured to releasably attach to the front of the article, partially encircling a user's waist when being worn. In other configurations, diapers have also been constructed containing an elastic waistband that also partially encircles the waist of a user.

The amount of stretch and elasticity present in an absorbent article in the transverse direction can have a significant impact upon the perceived comfort and fit of the garment. For example, if the elastic portions of the article only elongate when relatively high forces are exerted on the article, consumers may perceive that the product will not fit correctly and may not provide room for any movement without irritation from the product. If the article, on the other hand, stretches under relatively low amounts of force, consumers may perceive that the product fit will degrade during wear and may result in leakage.

The above problems may become exacerbated in some applications when the stretch properties of the garment are irregular or non-uniform. For instance, products having elastic fasteners and non-elastic waistbands or having elastic waistbands with non-elastic fasteners can, under some circumstances, feel uncomfortable to a consumer. Specifically, these products may feel under some circumstances to have too much stretch or too little stretch.

In view of the above, a need currently exists for an improved absorbent article that is perceived by consumers to have the correct amount of stretch around the entire waist of the user. A need also exists for an absorbent article that has uniform stretch properties in the transverse direction for providing a better and more comfortable fit.

In the past, efforts have been undertaken to produce totally stretchable, form-fitting pant-like absorbent garments. For example, a stretchable absorbent garment is disclosed in PCT International Publication No. WO 02/34185 to Morman, et al., which is incorporated herein by reference. In the above reference, a pant-like absorbent garment is disclosed having a stretchable outer cover and a non-stretchable bodyside liner. In one embodiment, the outer cover is stretchable in the transverse direction. The non-stretchable bodyside liner is attached to a pair of highly stretchable side panels. The total elongation of the side panels in centimeters in a transverse direction is roughly equal to the elongation of the outer cover in centimeters in the transverse direction. Further, the side panels have a percentage transverse stretch equal to at least one-half of a percentage transverse stretch of the outer cover times the width of the outer cover divided by a total width of the side panels. In this manner, the outer cover may stretch freely without inhibiting the non-stretchable bodyside liner.

Although the above patent application has provided great advancements in the art, the present invention is directed to further improvements in absorbent articles having controlled transverse stretch properties, especially controlled properties along the waist region of the article.

SUMMARY OF THE INVENTION

In general, the present invention relates to disposable absorbent articles having carefully controlled stretch properties. For instance, the absorbent articles contain uniform stretch properties in the transverse direction resulting in an improved fit and appearance. In particular, absorbent articles made in accordance with the present invention include a waistband made from multiple pieces of material joined together. Each of the materials, however, are tailored to have matching stretch properties in terms of displacement or elongation. In this manner, the multi-piece waistband simulates and is perceived as a single and unitary piece of material for maximizing comfort, improving fit and improving appearance.

As used herein, a waistband extends at least partially around the circumference of the absorbent article. For example, in one embodiment, the waistband may extend over a first side panel, a waist region, and a second opposing side panel. In an alternative embodiment, the waistband may form an entire circumference around the article. The different zones in the waistband may be identified by where two different materials are attached together or where a first material is placed on a second material.

For instance, in one embodiment, the present invention is directed to an absorbent article comprising an outer cover made from an extendable material. The outer cover may be made, for instance, from a laminate. The laminate may contain a film layer and a nonwoven layer. In one particular embodiment, the outer cover may comprise a neck-bonded laminate. In addition to being extendable, the outer cover may also be elastic.

A bodyside liner is joined to the outer cover in a superimposed relation. Similar to the outer cover, the bodyside liner also comprises an extendable material. The chassis further includes an absorbent structure positioned in between the outer cover and the bodyside liner. The chassis includes a front region and a back region that define a waist opening therebetween opposite two leg openings.

A pair of opposing fastening devices associated with a pair of corresponding elastic side panels are joined to opposing longitudinal edges of the chassis adjacent the waist opening. The fastening devices are configured to secure the article around the waist of a wearer. In many applications, the elastic side panels are attached to the back region of the chassis and are configured to wrap around towards the front of a user. In this regard, the fastening devices are configured to be secured to the front region of the chassis. The fastening device, for instance, may be either a hook material or a loop material of a hook and loop fastener or may comprise an adhesive that secures to an adhesive receptive landing zone located on the front region of the chassis. The fastening device may be located directly on the elastic side panels. Alternatively, the fastening device may comprise a nonextendable material that is attached to an edge of a corresponding elastic side panel.

The absorbent article further defines an elastic waist region that is laterally aligned with the elastic side panels. In one embodiment, the waist region has an elongation that is within 25% of the elongation of the elastic side panels when the waist region and the side panels are placed under a lateral force ranging from about 300 g to about 1400 g, such as from about 300 g to about 1000 g and, in one embodiment, from about 300 g to about 700 g. The elastic side panels and the waist region each have an elongation of at least 10% when placed under a lateral force of 500 g.

In other embodiments, the waist region has an elongation that is within 15%, particularly within 10%, and in one embodiment, within 5% of the elongation of the elastic side panels when both components are placed under a lateral force as described above.

In the above embodiment, the elastic side panels and the waist region of the absorbent article are designed to have a matching elongation. In an alternative embodiment, however, the waist region and the side panels may have a matching displacement when placed under a given load. For example, the waist region may undergo a displacement that is within 25% of the total displacement of both elastic side panels when the waist region and the elastic side panels are placed under a lateral force ranging from about 300 g to about 1400 g, such as from about 300 g to about 1000 g, and, in one embodiment, from about 300 g to about 700 g. The elastic side panels and the waist region may each have a displacement of at least 10 millimeters when placed under a lateral force of 500 g.

In other embodiments, the waist region may undergo a displacement that is within 15%, particularly within 10%, and in one embodiment, within 5% of the total displacement of the elastic side panels when placed under a lateral force as described above.

In general, the waist region that is laterally aligned with the elastic side panels traverses across the chassis of the absorbent article. The stretch properties of the waist region may be derived completely from the chassis. For instance, the chassis may be made from a stretchable outer cover and/or a stretchable liner in a manner that produces the desired stretch characteristics. Alternatively, a waist elastic member may be incorporated into or otherwise secured to the chassis to provide the desired stretch properties in conjunction with the elastic side panels.

The elastic side panels can be made from any suitable elastic material. For instance, the elastic side panels may be made from a film or from an elastic nonwoven or elastic laminate. In one particular embodiment, for instance, the elastic side panels are made from a neck-bonded laminate.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
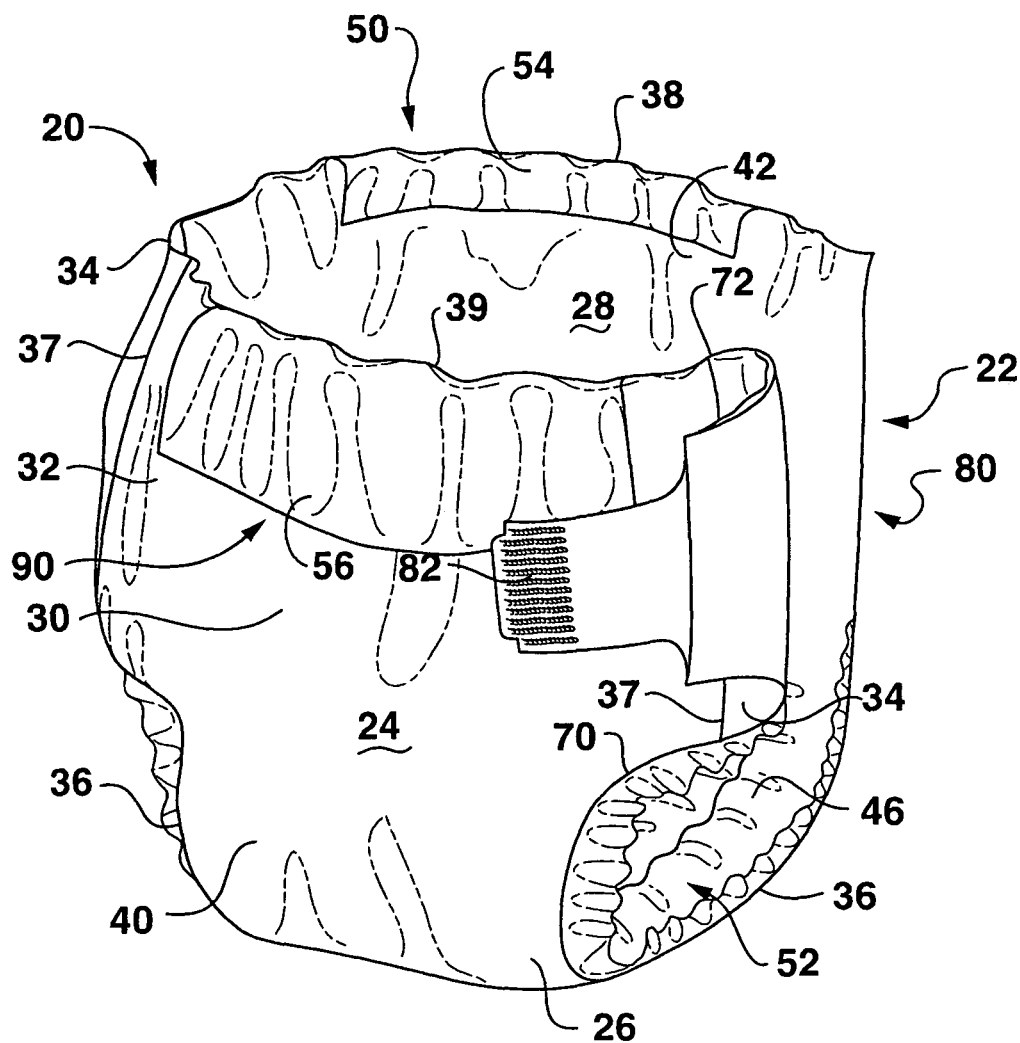
FIG. 1 is a rear perspective view of one embodiment of an absorbent article made in accordance with the present invention.

Repeated use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present invention is directed to absorbent articles, such as diapers, that contain a multi-component waistband with carefully controlled stretch properties. In particular, the products include a chassis having a front region and a back region that define a waist opening therebetween. The articles further include a crotch region positioned between the front and back region in the longitudinal direction and between a pair of leg openings in the lateral direction. Adjacent to the waist opening, the absorbent articles further include a pair of opposing elastic side panels, which, in some embodiments, may appear as elastic ears. The side panels may be attached to the chassis along a pair of opposing longitudinal edges. Alternatively, the side panels may be integrally formed with the chassis. A fastening device is located on or attached to each of the side panels.

When the articles are donned by a wearer, the side panels are extended around the waist of a wearer and the fastening devices are secured. For instance, in one embodiment, the elastic side panels are connected to the back region of the chassis and are extended over the front region of the chassis to secure the article in place on a wearer. Alternatively, the side panels may be attached to the front region of the chassis and are stretched around to the back of the chassis and secured in place.

The portion of the absorbent article that is laterally aligned with the elastic side panels comprises a waist region of the article. The waist region may be made up of the chassis itself or may include the chassis connected to one or more auxiliary elastic components. The side panels and the waist region of the article form a waistband. In accordance with the present invention, even though the waistband is made from multiple components, the waistband extends and contracts as a single piece of material. In particular, according to the present invention, the stretch properties of the elastic side panels are substantially matched with the stretch properties of the waist region of the article. In this manner, the entire waistband is perceived as a single piece of material providing the correct amount of stretch around the waist of the user. Ultimately, absorbent articles made in accordance with the present invention have an improved fit and allow for a relatively large range of sizes to use the article. Absorbent articles made in accordance with the present invention are also comfortable to wear and easily conform to the dimensions of a person's torso.

The manner in which the stretch properties of the elastic side panels are matched with the stretch properties of the waist region of the article may depend on various circumstances and the desired result. For instance, in one embodiment, the elongation of the side panels may be substantially matched with the elongation of the waist region for a given force range. In an alternative embodiment, however, the displacement that the side panels undergo over a given force range may be substantially matched with the amount of displacement that occurs in the waist region for the same range of forces. When the percent elongation of the side panels and the waist region are substantially the same, the two components have a similar elastic modulus individually. In the second case when the displacement of the components are substantially matched, the elastic modulus is varied in the components in order to have substantially the same displacement.

The range of forces over which the stretch properties of the side panels are matched with the stretch properties of the waist region can vary depending upon the particular absorbent article being produced and its end use. In general, however, the stretch properties of both the side panels and the waist region may be matched over a force range of from about 300 g to about 1400 g, and particularly from about 300 g to about 1000 g. In one embodiment, for instance, the stretch properties may be matched over a range of forces of from about 300 g to about 700 g. In an alternative embodiment, especially for adult products, the stretch properties of the side panels and the waist region may be matched over a force range of from about 800 g to about 4000 g. Waistbands on absorbent articles are typically exposed to forces within the above ranges.

How closely the stretch properties of the waist region and the stretch properties of the elastic side panels are matched may also vary depending upon the particular application. In general, the percent elongation of the waist region or the displacement of the waist region for a given force may be within about 25%, such as within about 15%, of the percent elongation or the displacement of the side panels over the same range of forces. For example, in one embodiment, the waist region may have a percent elongation or a displacement that is within about 10% or even within about 5% of the percent elongation or the displacement of the elastic side panels when the waist region and the side panels are placed under the same range of forces.

In general, the absorbent articles are made with extendable and/or elastic materials. As used herein, the term "extendable" refers to a material that may be extensible and/or elastic (or elastomeric). That is, the material may be extended, deformed or the like, without breaking, and may or may not significantly retract after removal of an extending force. The terms "elastic" or "elastomeric" are used interchangeably herein and refer to a property of a material where upon removal of an elongating force, the material is capable of recovering to substantially its unstretched size and shape or the material exhibits a significant retractive force. The term "extensible" refers to a property of a material where upon removal of an elongating force, the material experiences a substantially permanent deformation or the material does not exhibit a significant retractive force. In particular, elastic materials utilized in connection with the present invention may be elongated/extended or stretched in at least one direction without breaking by at least 15%, such as by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally advantageous that the elastomeric material or composite be capable of being elongated by at least 100%, more desirably at least 200%, of its relaxed length and recover at least 30% and more desirably 50% of its elongation upon release of a stretching, biasing force, within about one minute.

Figure 2:
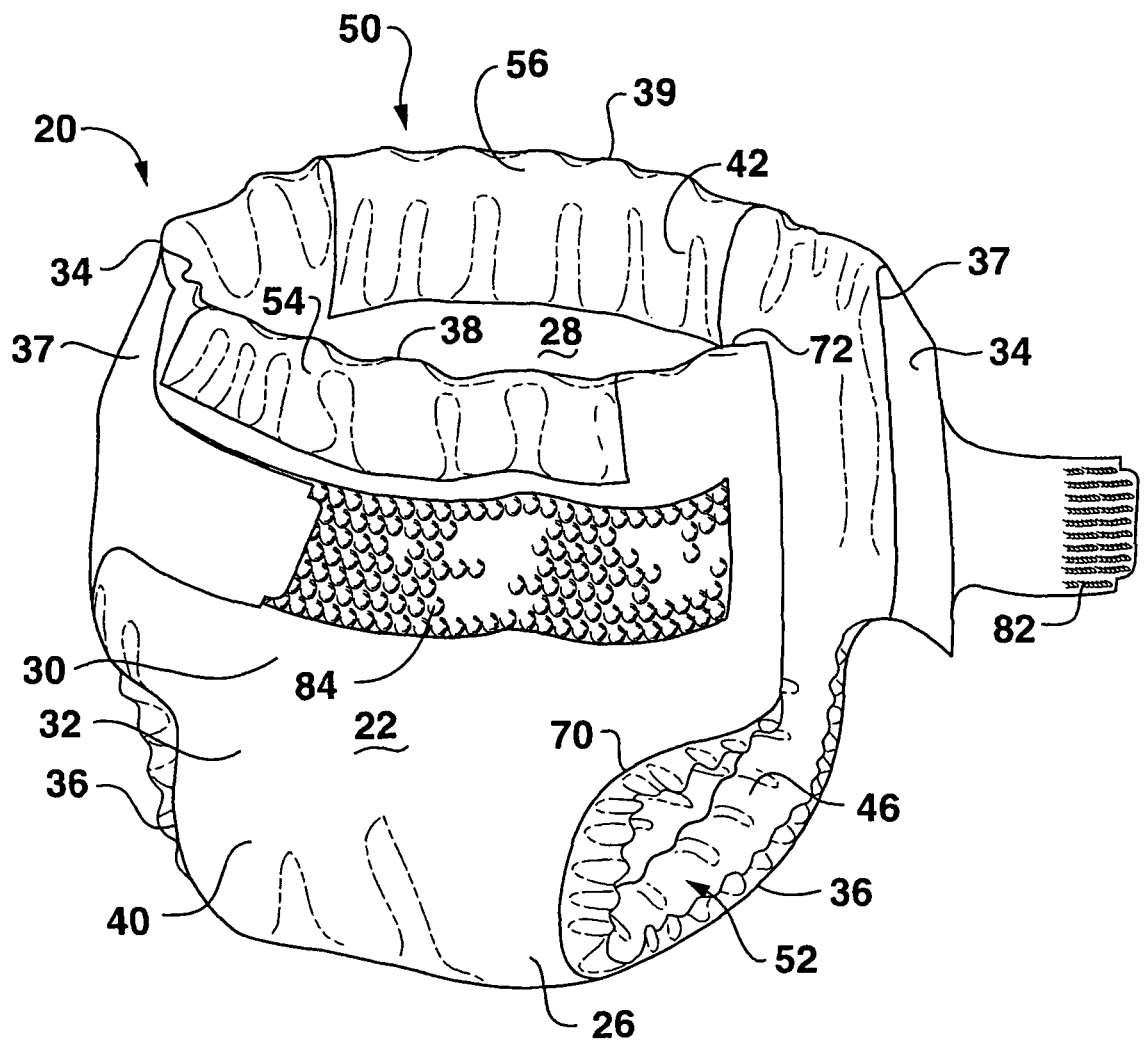
FIG. 2 is a front perspective view of the absorbent article illustrated in FIG. 1.

Referring to FIGS. 1 and 2, for exemplary purposes, an absorbent article 20 that may be made in accordance with the present invention is shown. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing absorbent articles such as the diaper 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
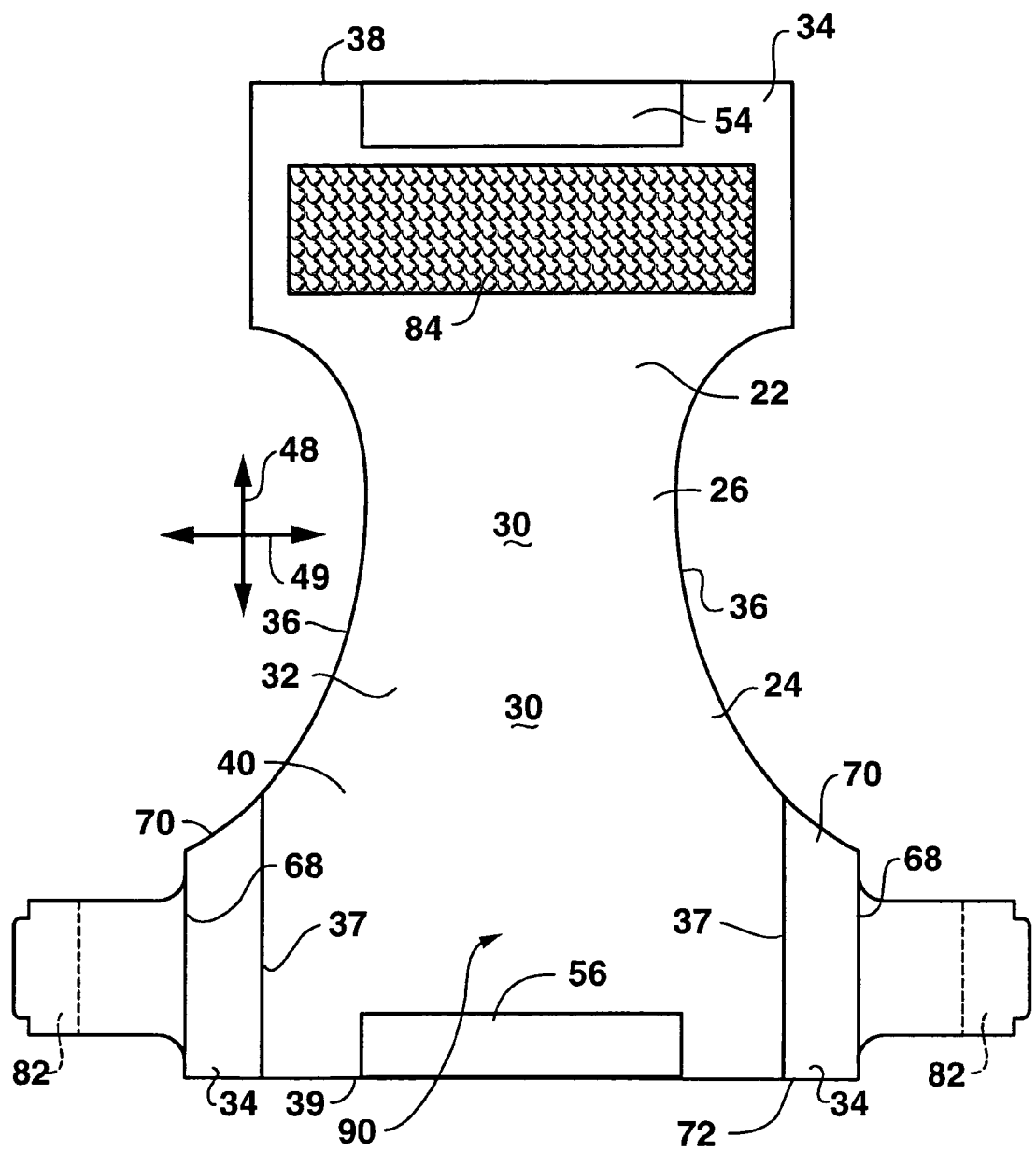
FIG. 3 is a plan view of the absorbent article shown in FIG. 1 with the article in an unfastened, unfolded and laid flat condition showing the surface of the article that faces away from the wearer.
Figure 4:
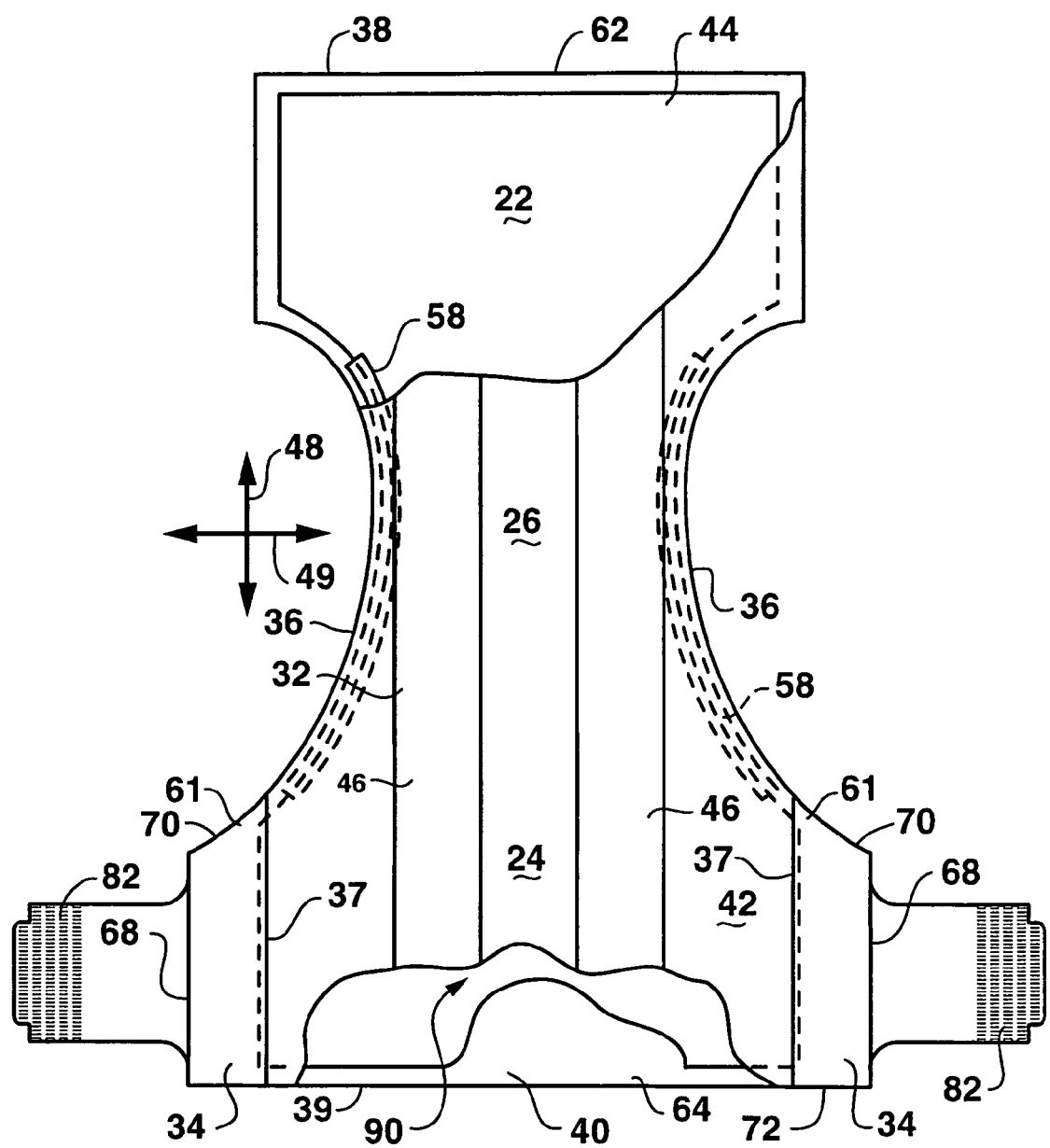
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32, that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 32 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

As described above, the present invention is particularly directed to absorbent articles having controlled and uniform stretch properties along the entire length of a waistband that extends from the outer edge of the first elastic side panel 34 to the outer edge of the second elastic side panel 34. The side panels 34 are elastic and extend in the lateral direction when the article is worn about a wearer. In addition to the side panels 34, the absorbent article 20 includes an elastic waist region generally 90 as particularly shown in FIGS. 1, 3 and 4 that is generally laterally aligned with the side panels 34 that traverses across the chassis 32. In the past, absorbent articles have been made with elastic side panels that have elastic properties much different than the waist region of the article. In order to improve fit and comfort, however, the present invention is directed to substantially matching the stretch properties of the elastic side panels 32 with the stretch properties of the waist region 90.

In one embodiment, for instance, the percent elongation of the side panels 34 over a particular range of forces is similar to or substantially equal to the percent elongation of the waist region 90 over the same range. For example, the absorbent article 20 may be constructed such that the waist region has an elongation that is within 25% of the elongation of the elastic side panels when the waist region and the side panels are placed under a lateral force ranging from about 300 g to about 700 g, such as from about 300 g to about 1000 g, and, in one embodiment, from about 300 g to about 1400 g. In other embodiments, the elongation of the waist region within the above range of forces may be within about 15%, such as within about 10%, and even within about 5% of the elongation of the elastic side panels. As used herein, the above comparisons are made between the waist region 90 and both side panels together 34.

By matching the stretch characteristics of the side panels in the waist region, strain is distributed uniformly over the entire waistband for improving the fit of the article.

In an alternative embodiment of the present invention, instead of matching percent elongation, the displacement of the waist region 90 substantially matches the total displacement of both side panels 34 over a given range of forces. In particular, the present inventors have discovered that in some embodiments it may be more desirable to match percent elongation, while in other embodiments, it may be more desirable to match total displacement. When matching displacement, for instance, the waist region undergoes a displacement that is within 25% of the total displacement of both elastic side panels when the waist region and the elastic side panels are placed under a lateral force ranging, for instance, from about 300 g to about 700 g, particularly from about 300 g to about 1000 g, and, in one embodiment, from about 300 g to about 1400 g. In an alternative embodiment, the range of forces may be from about 800 g to about 4000 g, such as when producing articles to be worn by adults. In various embodiments, the waist region may undergo a displacement that is within 15%, such as within 10%, and even within 5% of the total displacement of both elastic side panels under a given force range.

The materials used to construct the elastic side panels and the elastic waist region of the article may vary dramatically depending upon the particular application. In general, any suitable elastic material may be used in the absorbent article as long as the stretch characteristics of the side panels can be matched with the stretch characteristics of the waist region as described above. In general, the waist region and both side panels will have an elongation of at least 10% when placed under a lateral force of 500 g, such as at least 15%, and, in one embodiment, may have an elongation of at least 20% when placed under a force of 500 g. When placed under a force of about 500 g, both side panels and the waist region should also undergo a displacement of at least 10 millimeters, such as at least 15 millimeters for many applications.

Suitable elastic materials that may be used to construct the opposing side panels 34 are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly-necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference to the extent that they are consistent (i.e., not in conflict) herewith. Alternatively, the side panel material may include other woven or non-woven materials, such as those described later herein as being suitable for construction of the outer cover 40 and/or the bodyside liner 42; mechanically pre-strained composites; or stretchable but inelastic materials.

"Neck-bonded" laminate refers to a composite material having an elastic member that is bonded to a non-extensible member while the non-elastomeric member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Reversibly-necked material" refers to a necked material that has been treated while necked to impart memory to the material so that when force is applied to extend the material to it pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is described in U.S. Pat. Nos. 4,965,122 and 4,981,747, incorporated herein by reference for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,720,415, 4,789,699, 4781,966, 4,657,802, and 4,655,760, which are incorporated herein by reference in their entirety for all purposes.

"Neck stretch-bonded" laminate" refers to a laminate made from the combination of a neck-bonded laminate and a stretch-bonded laminate. Examples of necked stretch bonded laminates are disclosed in U.S. Pat. Nos. 5,114,781 and 5,116,662, which are incorporated herein in their entirety by reference thereto for all purposes. Of particular advantage, a necked stretch bonded laminate can be stretchable in both the machine and cross-machine directions.

In one particular embodiment, the elastic side panels or the chassis materials may comprise an elastic laminate, such as a neck-bonded laminate that may after formation be fed through a series of grooved rolls that have grooves in the cross machine direction. The grooved rolls, for instance, may increase the softness of the product.

The groove roll arrangement may be single rolls immediately adjacent one another such that the peaks of one roll lie in the valleys of an adjacent roll, or alternatively, they may be a single or main anvil roll that is encircled by smaller satellite rolls.

Similar to the elastic side panels 34, the waist region 90 of the absorbent article 20 can also be made from various different materials. The waist region 90, in many embodiments, at least contains portions of the outer cover 40, the inner liner 42, and possibly a portion of the absorbent structure 44. In addition, the waist region 90 can contain various elastic auxiliary components in order to control the stretch properties of the waist region. For instance, in the embodiment shown in FIGS. 1-4, the waist region 90 includes a waist elastic member 56 that is attached to the chassis 32. The waist elastic member 56, for instance, can be made from any of the materials described above. As shown in FIG. 1, the absorbent article 20 can include not only a back waist elastic member 56, but also a front waist elastic member 54. When present, the front waist elastic member 54 may constitute another extendable and elastic transverse section of the article.

In an alternative embodiment as shown in FIG. 4, the waist region 90 is comprised essentially of the chassis 32 and does not contain any auxiliary elastic components. In this embodiment, the stretch properties of the waist region 90 reside primarily in the outer cover 40 and the inner liner 42.

Figure 5:
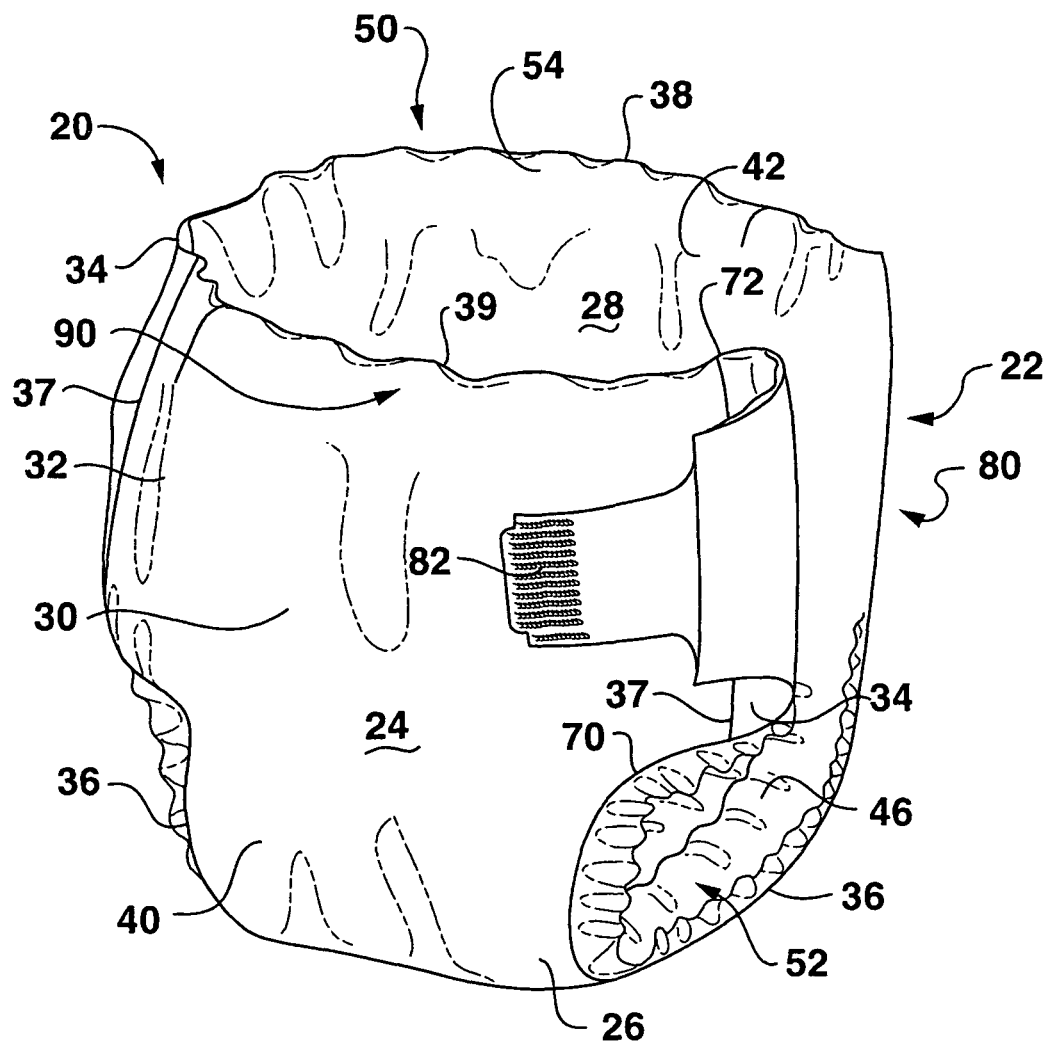
FIG. 5 is a rear perspective view of another embodiment of an absorbent article made in accordance with the present invention.

In many applications, the chassis 32 within the waist region 90 is at least extendable. Various auxiliary elastic components may then be incorporated into the chassis, such as waist elastic member 56, in order to make the waist region 90 elastic. In addition to being extendable, the chassis 32 may also be elastic such as in the embodiment shown in FIG. 5. For the chassis 32 to be elastic, the outer cover 40 may be elastic while the inner liner 42 may be extendable, the outer cover 40 may be extendable and the inner liner 42 may be elastic, or both the outer cover 40 and the inner liner 42 may be made from elastic materials. In still other embodiments, the absorbent structure 44 may be elastic and extend into the waist region 90.

Thus, the outer cover 40, the inner liner 42 and the absorbent structure 44 may be made from many different materials depending upon the particular application and the desired result. All three layers, for instance, may be extendable and/or elastic. Further, the stretch properties of each layer may vary in order to control the overall stretch properties of the product.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The outer cover 40 may be extendable and optionally elastic. Elastic non-woven laminate webs that can be used as the outer cover 40 include a non-woven material joined to one or more gatherable non-woven webs, films, or foams. Stretch Bonded Laminates (SBL) and Neck Bonded Laminates (NBL) are examples of elastomeric composites. Non-woven fabrics are any web of material which has been formed without the use of textile weaving processes which produce a structure of individual fibers that are interconnected in an integrating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, meltblown fabrics or spunbond fabrics composed of polyethylene, polypropylene, or polyolefin elastomers, as well as combinations thereof. The elastomeric materials may include PEBAX elastomer (available from AtoChem located in Philadelphia, Pa.), HYTREL elastomeric polyester (available from Invista of Wilmington, Del.), KRATON elastomer (available from Kraton Polymers of Houston, Tex.), or strands of LYCRA elastomer (available from Invista of Wilmington, Del.), or the like, as well as combinations thereof. The outer cover 40 may include materials that have elastomeric properties through a mechanical process, printing process, heating process, or chemical treatment. For examples such materials may be apertured, creped, neck-stretched, heat activated, embossed, and microstrained; and may be in the form of films, webs, and laminates.

In particular aspects of the invention, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by Bostik Findley Adhesive and designated as H2525A, and the elastomer strands are placed and distributed to provide approximately 12 strands of KRATON elastomer per inch (2.54 cm) of lateral width of the outer cover 40.

Alternatively, the outer cover 40 may include a woven or non-woven fibrous web layer which has been totally or partially constructed or treated to impart the desired levels of liquid impermeability to selected regions that are adjacent or proximate the absorbent structure. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate material composed of a 0.6 mil (0.015 mm) thick polypropylene blown film and a 0.7 osy (23.8 gsm) polypropylene spunbond material (2 denier fibers).

Suitable materials for a biaxially stretchable outer cover 40 include biaxially stretchable material and biaxially elastic stretchable material. One example of a suitable outer cover material can include a 0.3 osy (10.2 gsm) polypropylene spunbond that is necked 60% in the lateral direction 49 and creped 60% in the longitudinal direction 48, laminated with 3 grams per square meter (gsm) Findley 2525A styrene-isoprene-styrene based adhesive to 8 gsm PEBAX 2533 film with 20% $TiO_2$ concentrate. The outer cover 40 can suitably be stretched, laterally and/or longitudinally, by at least 30% (to at least 130% of an initial (unstretched) width and/or length of the outer cover 40). More suitably, the outer cover 40 can be stretched laterally and/or longitudinally, by at least 50% (to at least 150% of the unstretched width or length of the outer cover 40). Even more suitably, the outer cover 40 can be stretched, laterally and/or longitudinally, by at least 100% (to at least 200% of the unstretched width or length of the outer cover 40). Tension force in the outer cover 40 at 50% extension is suitably between 50 and 1000 grams, more suitably between 100 and 600 grams, as measured on a 3 inch (7.62 cm) wide piece of the outer cover material.

Another example of a suitable material for a biaxially stretchable outer cover 40 is a breathable elastic film/non-woven laminate, described in U.S. Pat. No. 5,883,028, issued to Morman et al., incorporated herein by reference to the extent that it is consistent (i.e. not in conflict) herewith. Examples of materials having two-way stretchability and retractability are disclosed in U.S. Pat. No. 5,116,662 issued to Morman and U.S. Pat. No. 5,114,781 issued to Morman, both of which are hereby incorporated herein by reference to the extent that it is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

In another embodiment, the outer cover 40 is made by adhesively laminating a facing material, such as a nonwoven web, to an extendable film followed by slit necking the material.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably includes a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials may be extensible biaxially stretchable materials, such as a neck stretched/creped spunbond. The bodyside liner 42 can also be made from extensible materials as are described in U.S. patent application Ser. No. 09/563,417 filed on May 3, 2000 by Roessler et al. The bodyside liner 42 can also be made from biaxially stretchable materials as are described in U.S. patent application Ser. No. 09/698,512 filed on Oct. 27, 2000 by Vukos et al.

The liner 42 can suitably be stretched, laterally and/or longitudinally, by at least 30% (to at least 130% of an initial (unstretched) width and/or length of the liner 42). More suitably, the liner 42 can be stretched laterally and/or longitudinally, by at least 50% (to at least 150% of the unstretched width or length of the liner 42). In some embodiments, the liner 42 can even be stretched, laterally and/or longitudinally, by at least 100% (to at least 200% of the unstretched width or length of the liner 42). Tension force in the liner 42 at 50% extension is suitably between 50 and 4000 grams, more suitably between 100 and 2000 grams, as measured on a 3 inch (7.62 cm) wide piece of the liner material.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. Nos. 4,100,324 to Anderson, et al.; 5,284,703 to Everhart, et al.; and 5,350,624 to Georger, et al.; which are incorporated herein by reference to the extent they are consistent (i.e., not in conflict) herewith.

In a particular aspect of the absorbent article of the present invention, the absorbent structure 44 may also be elastomeric. For this purpose, the absorbent web material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. These values may impact the absorbent structure 44 by affecting the desired levels of stretchability and structural stability without excessively degrading the physical properties or the liquid-management properties of the absorbent structure. An absorbent web material with an excessively low proportion of elastomeric fibers may be insufficiently stretchable, and a web material with an excessively high proportion of elastomeric fibers may exhibit an excessive degradation of its absorbency functionalities, such as poor intake, poor distribution, poor retention of liquid.

The absorbent structure 44 may include an elastomeric coform absorbent web material. Such materials are described for instance in U.S. Pat. Nos. 6,231,557 B1 and 6,362,389 B1, which are each incorporated by reference herein to the extent they are consistent (i.e., not in conflict) herewith. In particular aspects, the elastomeric coform material can have an overall coform basis weight of at least about 50 gsm, such as up to about 1200 gsm. The coform basis weight, for example, may be at least about 100 gsm, such as at least about 200 gsm. These values can provide the absorbent structure with the desired stretchability and structural stability without excessively degrading the physical properties or the liquid-management functionalities of the absorbent structure. For example, retention portions having excessively low proportions of elastomeric coform material may not be sufficiently stretchable. Conversely, an absorbent web material having excessively large amounts of elastomeric coform materials can exhibit an excessive degradation of their absorbency functionalities, such as an excessive degradation of intake, distribution and/or retention properties.

Other examples of usable elastomeric absorbent bodies are described in international patent application WO 03/051254 and U.S. Pat. Nos. 5,964,743, 5,645,542, 6,231,557, and 6,362,389 B1, each of which are incorporated by reference herein to the extent they are consistent (i.e., not in conflict) herewith.

Testing Procedures

For the purposes of the present invention, the properties, such as elongation, of a material or component can be determined by ASTM Procedure D 2433 "Standard Test Methods for Rubber Thread". Sections 20-22 of the ASTM Standard may be referred to for tensile strength testing.

A suitable testing device is a SINTECH constant rate of extension tensile tester (available from MTS Systems Corporation, a business having offices located in Edens Prairie, Minn.), or an equivalent device. The tensile tester is operatively programmed with suitable software, such as TESTWORKS software (available from MTS Systems Corporation), or an equivalent software.

Figure 6:
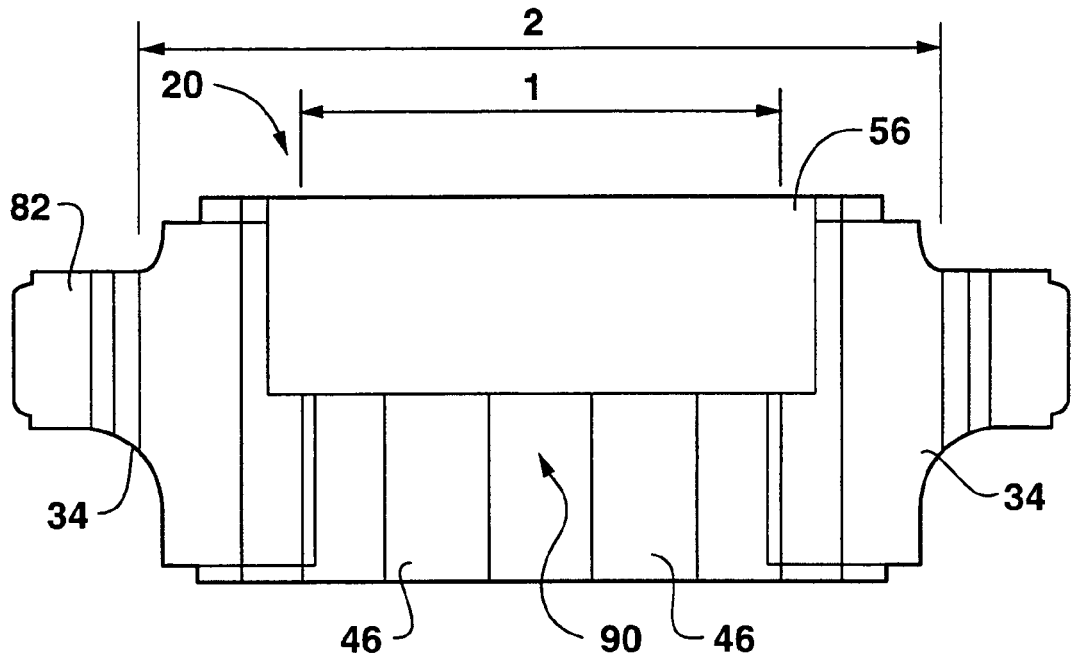
FIGS. 6 and 7 are plan views of portions of an absorbent article and is provided for illustrating a manner in which the stretch properties of an article may be determined.
Figure 7:
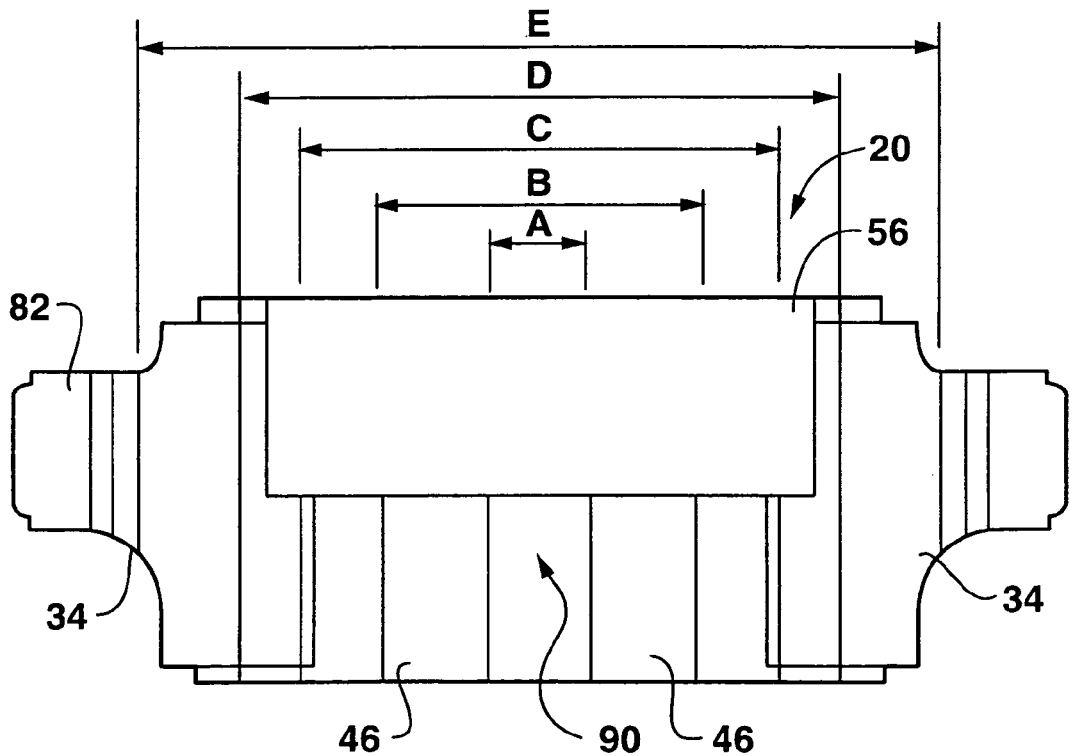

In order to test absorbent articles to determine if the articles have stretch properties within the scope of the present invention, the following procedure is offered with reference to FIGS. 6 and 7. In general, the following test procedure determines the stretch profile of a waistband of an absorbent article by measuring individual zones. For example, referring to FIG. 6, a portion of an absorbent article generally 20 is illustrated. In particular, shown in FIG. 6 is a rear waistband that extends from a first side panel 34 through a middle region 90 of the article and to a second side panel 34. As shown, the absorbent article 20 can include a waist elastic member 56 and containment flaps 46. The article 20 further includes fastening components 82 that are not included in the test, since, in this embodiment, they are non-elastic.

In order to measure the stretch properties of the article, as shown in FIG. 6, the waistband is first divided into two separate zones identified as zones 1 and 2. The zones are measured and recorded in millimeters at the product's resting state. The zone 2 measurement provides the gauge length for a constant rate of extension tensile machine. The resting state measurements are taken when the waistband is laid out flat but with no tension applied.

The waistband is then placed under incremental amounts of tension. For example, in accordance with the present invention, the waistband is first placed under a lateral force of 300 g. The lateral force is then increased by, for instance, 100 g until a desired end point is reached, such as about 700 g. After each increment, each zone is measured and the data is recorded in millimeters. If done manually, it may take up to about 45 seconds to take the measurements. In other embodiments, however, the measurements may be done almost instantaneously with the use of camera.

In some embodiments, testing may continue until a force of 1400 g or greater on the article.

Based upon the above procedure, the following data may be obtained:

| Amount of Force | Length of Zone 1 | Length of Zone 2 | Zone 2 Minus Zone 1 |
| --- | --- | --- | --- |
| 0 g | | | |
| 300 g | | | |
| 400 g | | | |
| 500 g | | | |
| 600 g | | | |
| 700 g, etc. | | | |

Displacement of the side panels 34 are represented by subtracting zone 2 from zone 1.

From the above data, percent elongation of the waist region 90 and the side panels 34 may be calculated. Percent elongation is calculated by subtracting the final length minus the initial length, dividing by the initial length, and multiplying by 100. This information can then be used to determine whether or not the elongation of the middle region 90 indicated as zone 1 is similar to the elongation of the side panels 34, which may be represented by zone 2 minus zone 1.

The above data can also be used to calculate displacement. Displacement is simply the final length minus the initial length. From this information, one can determine if the displacement of the side panels 34 substantially matches the displacement of the middle region 90 as discussed and defined herein.

In addition to determining the stretch characteristics of the side panels 34 in relation to the middle region 90, the above test may also be used to determine the similarities of stretch properties between different regions of the article. For instance, referring to FIG. 7, the absorbent article is shown divided into more zones, namely five zones designated A, B, C, D and E. Zone A represents a zone between the containment flaps, while zone B represents a zone bordered by the outer containment flap edges. Zone C, as discussed above, represents the middle region 90. Zone D, on the other hand, is where bonding of the side panels 34 ends. Zone E represents the entire width of the waistband. By dividing the article into more zones, the elastic properties of various regions may be compared and contrasted in designing products. For instance, percent elongation may be matched between the individual regions or, alternatively, displacement may be substantially matched between the individual regions.

In calculating percent elongation or displacement for any of the zones included in FIG. 7, data is first collected for each zone as the amount of tension placed on the article is increased, similar to the table presented above. In order to determine percent elongation or displacement for a particular section or region of the absorbent article 20, the data obtained from the individual zones may need to be manipulated. For instance, as described above with respect to FIG. 6, measurements taken with respect to zone 1 were subtracted from the measurements taken from zone 2 in order to particularly calculate percent elongation and displacement for the side panels.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
   a chassis including an outer cover comprising an extendable material, a bodyside liner joined to the outer cover in a superimposed relation, the bodyside liner also comprising an extendable material, and an absorbent structure positioned in between the outer cover and the bodyside liner, the chassis including a front region and a back region that define a waist opening therebetween opposite two leg openings;
   a pair of opposing fastening devices associated with a pair of corresponding elastic side panels, the elastic side panels being joined to opposing longitudinal edges of the chassis adjacent to the waist opening, the fastening devices for securing the article around the waist of a wearer; and
   wherein the absorbent article defines an elastic waist region that is generally aligned with the elastic side panels, the waist region having a percent elongation that is within 25% of the percent elongation of the elastic side panels when the waist region and the side panels are placed under a lateral force ranging from about 300 g to about 700 g, the waist region having a different elastic modulus than the elastic side panels and wherein the elastic side panels and the waist region each have an elongation of at least 10% when placed under a lateral force of 500 g.

2. An absorbent article as defined in claim 1, further comprising at least one waist elastic member positioned within the waist region of the article.

3. An absorbent article as defined in claim 1, wherein the elastic side panels are joined to opposing edges of the back region of the chassis, the waist region of the absorbent article being located along the back region of the chassis.

4. An absorbent article as defined in claim 3, wherein the pair of elastic side panels are configured to extend over the front region of the chassis, the fastening devices located on the side panels being configured to attach to the front region.

5. An absorbent article as defined in claim 1, wherein the elastic side panels comprise a neck-bonded laminate.

6. An absorbent article as defined in claim 1, wherein the outer cover, bodyside liner, or both the outer cover and the bodyside liner are substantially responsible for the elongation properties of the waist region of the article.

7. An absorbent article as defined in claim 1, wherein the waist region of the absorbent article does not contain any auxiliary elastic components attached to the chassis.

8. An absorbent article as defined in claim 1, wherein the percent elongation of the waist region is within 15% of the percent elongation of the elastic side panels when the waist region and the elastic side panels are placed under a lateral force ranging from about 300 g to about 700 g.

9. An absorbent article as defined in claim 1, wherein the percent elongation of the waist region is within 10% of the percent elongation of the elastic side panels when the waist region and the elastic side panels are placed under a lateral force ranging from about 300 g to about 700 g.

10. An absorbent article as defined in claim 1, wherein the percent elongation of the waist region is within 5% of the percent elongation of the elastic side panels when the waist region and the elastic side panels are placed under a lateral force ranging from about 300 g to about 700 g.

11. An absorbent article as defined in claim 1, wherein the percent elongation of the waist region is within 25% of the percent elongation of the elastic side panels when the waist region and the side panels are placed under a lateral force ranging from about 300 g to about 1000 g.

12. An absorbent article as defined in claim 1, wherein the percent elongation of the waist region is within 25% of the percent elongation of the elastic side panels when the waist region and the side panels are placed under a lateral force ranging from about 300 g to about 1400 g.

13. An absorbent article as defined in claim 1, wherein both the waist region and the elastic side panels have an elongation of at least 20% when placed under a lateral force of 500 g.

14. An absorbent article as defined in claim 1, wherein both the waist region and the elastic side panels have an elongation of at least 30% when placed under a lateral force of 500 g.

15. An absorbent article as defined in claim 1, wherein the outer cover comprises an extendable laminate, the laminate containing a film and a nonwoven material or comprises a neck-bonded laminate.

16. An absorbent article as defined in claim 1, wherein the absorbent structure floats in between the outer cover and the bodyside liner.

17. An absorbent article as defined in claim 1, wherein at least a portion of the absorbent structure floats in between the outer cover and the bodyside liner.

18. An absorbent article comprising:
a chassis including an outer cover comprising an extendable material, a bodyside liner joined to the outer cover in a superimposed relation, the bodyside liner also comprising an extendable material, and an absorbent structure positioned in between the outer cover and the bodyside liner, the chassis including a front region and a back region that define a waist opening therebetween opposite two leg openings;
a pair of opposing fastening devices associated with a pair of corresponding elastic side panels, the elastic side panels being joined to opposing longitudinal edges of the chassis adjacent to the waist opening, the fastening devices for securing the article around the waist of a wearer; and
wherein the absorbent article defines an elastic waist region that is generally aligned with the elastic side panels, the waist region undergoing a displacement that is within 25% of the total displacement of both elastic side panels when the waist region and the elastic side panels are placed under a lateral force ranging from about 300 g to about 700 g, the waist region having a different elastic modulus than the elastic side panels and wherein the elastic side panels and the waist region each have a displacement of at least 10 mm when placed under a lateral force of 500 g.

19. An absorbent article as defined in claim 18, further comprising at least one waist elastic member positioned within the waist region of the article.

20. An absorbent article as defined in claim 18, wherein the displacement of the waist region is within 15% of the total displacement of the elastic side panels when the waist region and the elastic side panels are placed under a lateral force ranging from about 300 g to about 700 g.

21. An absorbent article as defined in claim 18, wherein the displacement of the waist region is within 10% of the total displacement of the elastic side panels when the waist region and the elastic side panels are placed under a lateral force ranging from about 300 g to about 700 g.

22. An absorbent article as defined in claim 18, wherein the displacement of the waist region is within 5% of the total displacement of the elastic side panels when the waist region and the elastic side panels are placed under a lateral force ranging from about 300 g to about 700 g.

23. An absorbent article as defined in claim 18, wherein both the displacement of the waist region and the total displacement of the elastic side panels is at least about 15 mm when placed under a lateral force of 500 g.

24. An absorbent article as defined in claim 18, wherein the elastic side panels are joined to opposing edges of the back region of the chassis, the waist region of the absorbent article being located along the back region of the chassis.

25. An absorbent article as defined in claim 24, wherein the pair of elastic side panels are configured to extend over the front region of the chassis, the fastening devices located on the side panels being configured to attach to the front region.

26. An absorbent article as defined in claim 18, wherein the elastic side panels comprise a neck-bonded laminate.

27. An absorbent article as defined in claim 18, wherein the outer cover is elastic.

28. An absorbent article as defined in claim 18, wherein the waist region of the absorbent article does not contain any auxiliary elastic components attached to the chassis.

29. An absorbent article as defined in claim 18, wherein the waist region undergoes a displacement that is within 25% of the total displacement of both elastic side panels when the waist region and the elastic side panels are placed under a lateral force ranging from about 300 g to about 1000 g.

30. An absorbent article as defined in claim 18, wherein the waist region undergoes a displacement that is within 25% of the total displacement of both elastic side panels when the waist region and the elastic side panels are placed under a lateral force ranging from about 300 g to about 1400 g.

31. An absorbent article as defined in claim 18, wherein the outer cover comprises an extendable laminate, the laminate containing a film and a nonwoven material or comprises a neck-bonded laminate.

32. An absorbent article as defined in claim 18, wherein the absorbent structure floats in between the outer cover and the bodyside liner.

33. An absorbent article as defined in claim 18, wherein at least a portion of the absorbent structure floats in between the outer cover and the bodyside liner.

34. An absorbent article comprising:
- a chassis including an outer cover comprising an extendable material, a bodyside liner joined to the outer cover in a superimposed relation, the bodyside liner also comprising an extendable material, and an absorbent structure positioned in between the outer cover and the bodyside liner, the chassis including a front region and a back region that define a waist opening therebetween opposite two leg openings;
- a pair of opposing fastening devices associated with a pair of corresponding elastic side panels, the elastic side panels extend laterally from the chassis adjacent to the waist opening, the fastening devices for securing the article around the waist of a wearer; and
- wherein the absorbent article defines a waistband that extends in a transverse direction at least over the front region or the back region of the chassis, the waistband being capable of being divided into at least a first and a second zone, the first zone having a percent elongation or a displacement that is within 25% of the percent elongation or the displacement of the second zone respectively when the waistband is placed under a lateral force ranging from about 300 g to about 700 g, the first zone having a different elastic modulus from the second zone and wherein each zone has an elongation of at least 10% when placed under a lateral force of 500 g.

35. An absorbent article as defined in claim 34, wherein the waistband comprises an elastic waist region as a first zone and a pair of elastic side panels as a second zone.

36. An absorbent article as defined in claim 34, wherein the waistband forms a complete circumference around the absorbent article parallel to the waist opening.

37. An absorbent article as defined in claim 34, wherein the elastic side panels are integral with the chassis.

38. An absorbent article as defined in claim 34, wherein the elastic side panels are joined to opposing longitudinal edges of the chassis.

39. An absorbent article as defined in claim 34, wherein the waistband is capable of being divided into more than two zones and wherein each zone has a percent elongation or a displacement that is within 25% of the percent elongation or the displacement of the other zones respectively when the waistband is placed under a lateral force ranging from about 300 g to about 700 g.

* * * * *